United States Patent
Waheed

(10) Patent No.: US 6,212,684 B1
(45) Date of Patent: Apr. 10, 2001

(54) STRAIT JACKET

(76) Inventor: Keith Waheed, 418 Southeast 8th St. No. 12, Hallandale, FL (US) 33009

( * ) Notice: Subject to any disclaimer, the term of this patent is extended or adjusted under 35 U.S.C. 154(b) by 0 days.

(21) Appl. No.: 09/658,601

(22) Filed: Sep. 8, 2000

(51) Int. Cl.[7] ............................. A61F 5/37; A41B 11/112
(52) U.S. Cl. ............................. 2/69; 2/115; 2/85; 2/108; 128/873; 128/874
(58) Field of Search ................................... 2/69, 115, 114, 2/108, 106, 105, 93, 85, 83, 80, 95; 128/846, 869, 870, 873, 874, 876; 297/464, 465

(56) References Cited

U.S. PATENT DOCUMENTS

| 2,664,083 | 12/1953 | Heymans . | | |
|---|---|---|---|---|
| 2,769,177 | 11/1956 | Berg . | | |
| 3,407,807 | 10/1968 | Giberson . | | |
| 3,502,073 | 3/1970 | Stanley . | | |
| 3,901,229 | 8/1975 | Hensel et al. . | | |
| 5,031,639 | 7/1991 | Wolfer . | | |
| 5,267,352 | * | 12/1993 | Rodarmel | 2/44 |
| 6,024,091 | * | 2/2000 | Bennett | 128/873 |

FOREIGN PATENT DOCUMENTS 459200   4/1949   (CA) .

* cited by examiner

*Primary Examiner*—Gloria M. Hale
(74) *Attorney, Agent, or Firm*—Stephen R. Greiner

(57) ABSTRACT

A strait jacket including a front panel for positioning against the chest of a wearer and a rear panel for positioning against the back of a wearer. The front panel is disguised to look like the front of a conventional jacket. The rear panel is divided into side-by-side parts and has a releasable fastener joining these parts together. A pair of tubular sleeves for receiving the arms of a wearer is joined to the front and back panels and extends therefrom. The sleeves are sewn to the front panel so that a wearer cannot raise such.

9 Claims, 1 Drawing Sheet

STRAIT JACKET

FIELD OF THE INVENTION

The present invention relates generally to restraining devices of vest or shirt type for the upper torso of a wearer.

BACKGROUND OF THE INVENTION

According to a recent Justice Department report, the number of people held in U.S. prisons, jails and other correctional facilities exceeded two million at the end of 1999. On any given day, thousands of these people are being transported between these facilities or to various courts. For long distance trips, commercial carriers and public accommodations are often used.

While being transported and during court appearances, prisoners are usually restrained by handcuffs binding their wrists together for the safety of those nearby. Because handcuffs permit a prisoner to elevate his arms, a belt with a handcuff-retaining loop is normally also fastened about the waist of the prisoner. When the cuffs are passed through the loop, the prisoner is effectively prevented from moving his hands, wrists, arms and elbows more than a few inches in any one direction.

Unfortunately, there are problems associated with "locking down" a prisoner by means of handcuffs and a retaining belt. When worn for long periods, handcuffs tend to dig into the skin of a wearer, restricting blood flow to the hands and sometimes causing cuts, bruises, and great discomfort. Of course, to eat or use the restroom, a prisoner must be uncuffed—conduct that violates the rules of most airlines, restaurants, and hotels and is grounds for expulsion therefrom. Finally, the sight of a handcuffed person is frightening to some and may cause onlookers to panic or flee from this person's presence. A need, therefore, exists for a product that permits control over the movements of a prisoner while in public places to be maintained at all times yet is unobtrusive and unnoticeable to casual observers.

SUMMARY OF THE INVENTION

In light of the problems associated with the known methods and apparatus for transporting prisoners from place to place using commercial carriers and other public accommodations, it is a principal object of the invention to provide a garment having the appearance of a regular jacket that will immobilize the upper body of a wearer. The garment selectively pins the arms of a wearer to his torso and positions his hands in the same location that handcuffs and a retaining belt would. The garment is safe, unobtrusive, and offers a level of security believed to be equal to that of handcuffs.

It is another object of the present invention to provide a garment that is not only useful in securely transporting prisoners from place to place but, when employed in a courthouse in the presence of a judge or jury, can reduce or eliminate any stigma or assumption of guilt associated with the wearing of handcuffs. In short, the wearer of the garment does not appear to be dangerous on account of the garment.

It is a further object of the invention to provide a garment that can be made in practically any size to accommodate wearers of different statures. Whatever the size, however, the garment is compact. When not in use, it may be easily carried, folded away in a piece of luggage or suspended from a hanger in a closet.

It is an additional object of the invention to provide a garment of the type described that may be easily donned or doffed with the help of an assistant. Once positioned on a wearer, however, the wearer, being incapable of moving his arms, cannot remove the garment without the assistant's aid.

It is an additional object of the invention to provide a garment for the restraint of a wearer that is comfortable to wear, having no hard parts that can rub against the skin of a wearer. Thus, the likelihood of injury to a wearer caused by the garment is minimal.

It is another object of the invention to provide a restraining garment that does not have to be fully removed to permit a wearer to eat or relieve himself. It is believed, then, that airlines and other public providers of services will be less likely to shun wearers of the garment from their facilities.

It is an object of the invention to provide improved elements and arrangements thereof in a garment being a strait jacket for the purposes described which is lightweight in construction, inexpensive to manufacture, and dependable in use.

Briefly, the strait jacket in accordance with this invention achieves the intended objects by featuring a front panel and a rear panel with side-by-side parts. A zipper releasably fastens the side-by-side parts together. A pair of sleeves extend from the front and rear panels and are sewn to the front panel so that they cannot be raised. One of the sleeves has a lateral opening extending from its bottom that can be selectively closed with a zipper. A belt may be run through passageways formed between the sleeves and front panel to draw the sleeves rearwardly. A pair of cuffs are secured to the bottom of the sleeves and have releasable fasteners so that they can be adjusted in size.

The foregoing and other objects, features and advantages of the present invention will become readily apparent upon further review of the following detailed description of the preferred embodiment as illustrated in the accompanying drawings.

BRIEF DESCRIPTION OF THE DRAWINGS

The present invention may be more readily described with reference to the accompanying drawings, in which.

Similar reference characters denote corresponding features consistently throughout the accompanying drawings.

DETAILED DESCRIPTION OF THE PREFERRED EMBODIMENT

Figure 1:
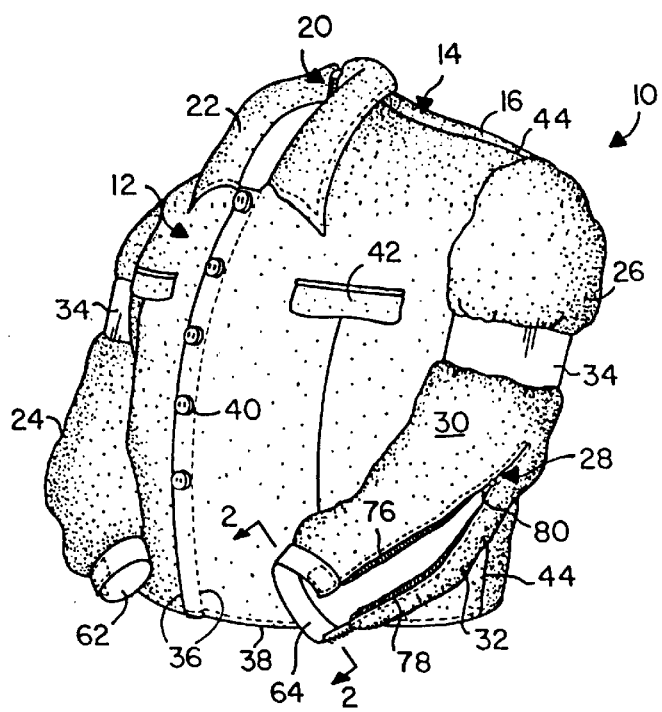
FIG. 1 is a perspective view of a strait jacket in accordance with the present invention.
Figure 2:
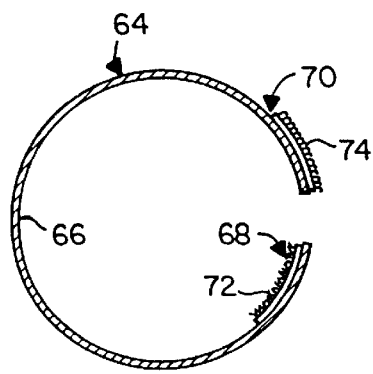
FIG. 2 is a cross-sectional view of the cuff of the strait jacket taken along line 2—2 of FIG. 1.

Referring now to the FIGS., a strait jacket in accordance with the present invention is shown at 10. Strait jacket 10 includes a front panel 12 for positioning against the chest of a wearer and a rear panel 14 for positioning against the back of a wearer. Front panel 12 is disguised to look like the front of a conventional jacket. Rear panel 14 is split into side-by-side parts 16 and 18 and has a zipper 20 joining parts 16 and 18 together. A collar 22 is connected to front and back panels 12 and 14 for encircling the neck of a wearer. A pair of tubular sleeves 24 and 26 for receiving the arms of a wearer are joined to the front and back panels 12 and 14 and extend therefrom. Sleeves 24 and 26 are stitched downwardly to front panel 12 so that a wearer cannot raise such.

Sleeve 24 is split and zipper 28 joins its adjacent parts 30 and 32 together. A belt 34 may be run around sleeves 24 and 26 to further draw such rearwardly toward back panel 14.

Strait jacket 10 is made from a durable fabric such as canvas. Front panel 12, back panel 14, collar 22, and sleeves 24 and 26 are cut to fit a wearer and are stitched together using conventional sewing techniques. Zippers 20 and 28 are hidden along their lengths by flaps formed from fabric comprising the adjacent parts 16, 18, 30 and 32. The resulting jacket has a normal appearance, attracting minimal attention from those viewing it.

Front panel 12 has a pair of vertical seams 36 spaced about one inch (2.5 cm) apart and extending down the center of front panel 12 from its top at collar 22 to its bottom at hem 38 that simulate the opening in a conventional jacket. Between seams 36, a number of buttons 40 are stitched onto front panel 12 to simulate means for closing the opening in a conventional jacket. False pocket flaps 42 are stitched to front panel 12 on opposite sides of seams 36 to complete the visual effect that jacket 10 is conventional in operation.

Parts 16 and 18 of rear panel 14 are sewn along their forward edges and at side seams 44 to front panel 12. The rearward edges of parts 16 and 18, however, are releasably secured to one another by the toothed fastening components 46 and 48 of zipper 20. Parts 16 and 18, being of equal size, locate zipper 20 in the center of rear panel 14. Fastening components 46 and 48 extend vertically downward from their tops at collar 22 to their bottoms at hem 38. A slidable tab 50 permits fastening components 46 and 48 to be selectively separated so that strait jacket 10 may be donned from the rear.

Figure 3:
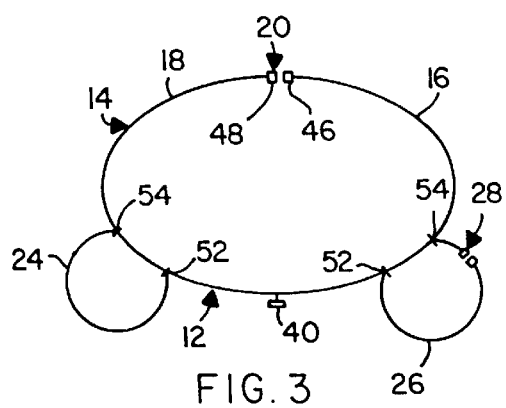
FIG. 3 is a diagrammatic horizontal cross-section of the strait jacket.
Figure 4:
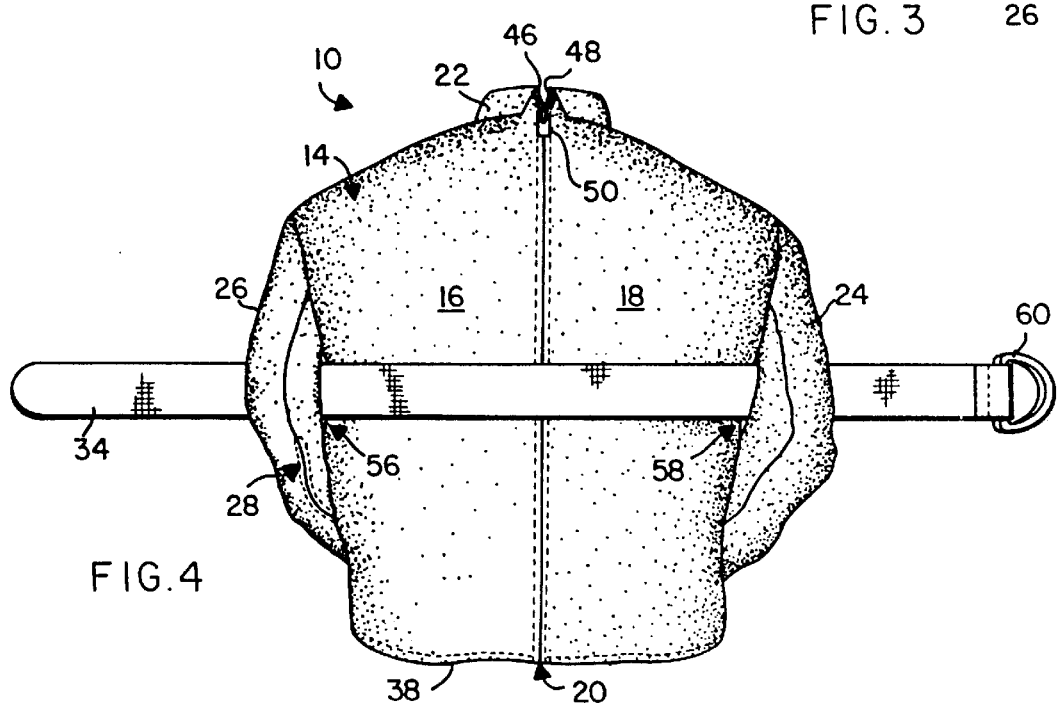
FIG. 4 is a rear view of the strait jacket.

Sleeves 24 and 26 are sewn about their upper ends to front and back panels 12 and 14 in the manner of a conventional jacket. Hidden seams 52 and 54, whose position is illustrated schematically in FIG. 3, fasten sleeves 24 and 26 to front panel 12 so that the lower ends of sleeves 24 and 26 terminate closely adjacent seams 36 and hem 38. Thus, a person wearing strait jacket 10 is forced to keep his hands adjacent his abdomen in the same location as a wearer of handcuffs.

Seams 52 and 54 extend upwardly from the lower end of sleeves 24 and 26 to about their midpoints, locations proximate the elbows of a wearer. By terminating seams 52 and 54 at a distance from the upper ends of sleeves 24 and 26, passageways 56 and 58 are formed between arms 24 and 26 and front panel 12. Belt 34 formed of flexible webbing may be extended through passageways 56 and 58 and around sleeves 24 and 26 after strait jacket 10 has been donned. A clasp 60 is provided at one end of belt 34 for connecting the ends of belt 34 firmly together adjacent rear panel 14 to further restrict movement of the arms of the wearer of strait jacket 10.

Sleeves 24 and 26 terminate with cuffs 62 and 64 sewn to their lower ends. Each cuff 62 and 64 includes a fabric strip 66 formed into a semicircle whose ends are adjacent one another. Hook and loop fasteners 68 and 70 are attached to the opposite ends of each strip 66. Fastener 68 is sewn to the inner face of strip 66 and comprises a strip of "Velcro" pile material including a dense mat of small, uncut loops 72 formed of thread. Fastener 70, however, is sewn to the outer face of strip 66 and comprises a strip of "Velcro" hook material having a plurality of transverse lines of hooks 74 spaced along its length. The ends of hooks 74 are turned inwardly so as to catch in loops 72 when fasteners 70 and 72 are pressed together thereby permitting each strip 66 to be formed into a band of adjustable size.

Toothed fastening components 76 and 78 extend upwardly from the gap between the adjacent ends of strip 66 along opposite edges of parts 30 and 32 to about the midpoint of sleeve 26. A slidable tab 80 permits fastening components 76 and 78 to be selectively separated so that one arm of a wearer may be selectively freed for eating or other activities like using a restroom. Even while zipper 28 is opened, the remainder of the upper body of a wearer of strait jacket 10 is substantially restrained.

The use of strait jacket 10 is straightforward. First, zipper 20 is opened, parts 16 and 18 are separated, and the arms of a wearer are inserted into sleeves 24 and 26 so that his hands extend from cuffs 62 and 64. By next drawing slidable tab 50 upwardly over fastening components 46 and 48, parts 16 and 18 are connected together with the wearer inside jacket 10. After that, belt 34 is fed through passageways 56 and 58 and around sleeves 24 and 26 and its ends are connected together adjacent rear panel 14 by means of clasp 60. Cuffs 62 and 64 are then secured against the wrists of a wearer by wrapping such around the wrists and pressing fasteners 68 and 70 together to maintain a tight fit. Should the wearer require the free use of one arm at some time, cuff 64 may be undone and zipper tab 80 drawn upwardly to open sleeve 26. At all other times, the wearer is restrained from moving his arms. To all but the most observant viewers, a wearer will appear to be entirely unconstrained by strait jacket 10.

When use of strait jacket 10 is no longer required, it is removed from a wearer by reversing the steps outlined above. The strait jacket 10 is then folded up or hung in a closet for storage and subsequent reuse. If necessary, strait jacket 10 may be washed with known detergents in a washing machine.

While the invention has been described with a high degree of particularity, it will be appreciated by those skilled in the art that modifications may be made thereto. For example, strait jacket 10 could be made with interior pockets to accommodate body armor for protecting prisoners at risk of attack. Also, strait jacket 10 could be made with a zipper 28 in both sleeves 24 and 26 so that both arms of a wearer may be selectively unbound. Therefore, it is to be understood that the present invention is not limited to the sole embodiment described above, but encompasses any and all embodiments within the scope of the following claims.

I claim:

1. A strait jacket, comprising:
    a front panel for positioning against the chest of a wearer;
    a rear panel joined to said front panel for positioning against the back of a wearer, said rear panel being split into side-by-side parts selectively joined together by a first releasable fastener; and,
    a pair of tubular sleeves joined to and extending from said front panel and said rear panel for receiving the arms of a wearer, said sleeves being sewn to said front panel so that a wearer cannot raise such and terminating adjacent a bottom thereof.

2. The strait jacket according to claim 1 wherein said first releasable fastener is a zipper.

3. The strait jacket according to claim 1 wherein one of said sleeves is provided with a lateral opening extending upwardly from its bottom to about its midpoint and said strait jacket further comprises a second releasable fastener for selectively closing said opening.

4. The strait jacket according to claim 3 wherein said second releasable fastener is a zipper.

5. The strait jacket according to claim 1 further comprising a belt extended around both of said sleeves for drawing such rearwardly toward said back panel.

6. A straitjacket, comprising:

a front panel for positioning against the chest of a wearer;

a rear panel joined to said front panel for positioning against the back of a wearer, said rear panel having side-by-side parts;

a first zipper on said rear panel for releasably fastening together said side-by-side parts of said rear panel;

a pair of tubular sleeves joined to and extending from said front panel and said rear panel for receiving the arms of a wearer, said sleeves being sewn to said front panel so that a wearer cannot raise such, said sleeves having bottoms positioned closely adjacent one another and a bottom of said front panel, and one of said sleeves having a lateral opening extending upwardly from its bottom to about its midpoint; and, a second zipper on said sleeve for selectively closing said lateral opening.

7. The strait jacket according to claim 6 further comprising:

a pair of passageways each being respectively positioned between one of said sleeves and said front panel; and, a belt extended through said passageways and around both of said sleeves for drawing such rearwardly toward said back panel.

8. The strait jacket according to claim 6 further comprising a pair of cuffs each being respectively secured to the bottom of one of said sleeves, each of said cuffs including:

a fabric strip formed into a semicircle and having opposite ends positioned adjacent one another; and, hook and loop fasteners attached to said opposite ends of each said strip permitting each said strip to be formed into a band of adjustable size.

9. A strait jacket, comprising:

a front panel for positioning against the chest of a wearer;

a rear panel joined to said front panel for positioning against the back of a wearer, said rear panel having side-by-side parts;

a first zipper on said rear panel for releasably fastening together said side-by-side parts of said rear panel;

a pair of tubular sleeves joined to and extending from said front panel and said rear panel for receiving the arms of a wearer, said sleeves being sewn to said front panel so that a wearer cannot raise such, said sleeves having bottoms positioned closely adjacent one another and a bottom of said front panel, and one of said sleeves having a lateral opening extending upwardly from its bottom to about its midpoint;

a second zipper on said sleeve for selectively closing said lateral opening;

a pair of passageways each being respectively positioned between one of said sleeves and said front panel;

a belt extended through said passageways and around both of said sleeves for drawing such rearwardly toward said back panel and, a pair of cuffs each being respectively secured to the bottom of one of said sleeves, each of said cuffs including:

a fabric strip formed into a semicircle and having opposite ends positioned adjacent one another; and, hook and loop fasteners attached to said opposite ends of each said strip permitting each said strip to be formed into a band of adjustable size.

\* \* \* \* \*